United States Patent [19]

Pruitt

[11] Patent Number: 4,975,108

[45] Date of Patent: Dec. 4, 1990

[54] CONTROLLED RELEASE COMPOSITION AND METHOD OF MANUFACTURING SAME

[76] Inventor: Norman W. Pruitt, 3501 Launcelot Way, Annandale, Va. 22003

[21] Appl. No.: 769,082

[22] Filed: Aug. 26, 1985

[51] Int. Cl.$^5$ .......................... C05G 3/00; C05G 3/02; C05G 3/04; C05F 5/00

[52] U.S. Cl. .......................................... 71/23; 71/65; 71/79; 71/DIG. 1; 71/64.13; 71/904; 34/10; 47/58; 514/1; 514/769; 514/772

[58] Field of Search ..................... 71/1, 23, 904, 64.13; 471/65, 79, DIG. 1; 514/1, 769, 772; 47/58; 34/10

[56] References Cited

U.S. PATENT DOCUMENTS 3,017,720 1/1962 Busch ................................. 71/904 X

OTHER PUBLICATIONS

CA 75(21): 128815k, Rauscher et al., "Pesticides on Porous Fiber Carriers", 1971.
CA 83(26): 207785o, Hedstrom, "Apparatus and Method for Drying Cellulose Pulp", 1975.

Primary Examiner—Ferris H. Lander
Attorney, Agent, or Firm—A. W. Breiner

[57] ABSTRACT

Controlled release compositions are manufactured by subjecting cellulosic pulp rejects to a dewatering operation to remove approximately 25% of the water; flash-drying the obtained partially dewatered rejects, causing the rejects to expand and become porous; adding an additive material to impregnate the expanded and porous cellulosic material, and drying. The cellulosic material holds or retains the additive for delayed release. The compositions have good stability and structural integrity.

18 Claims, 1 Drawing Sheet

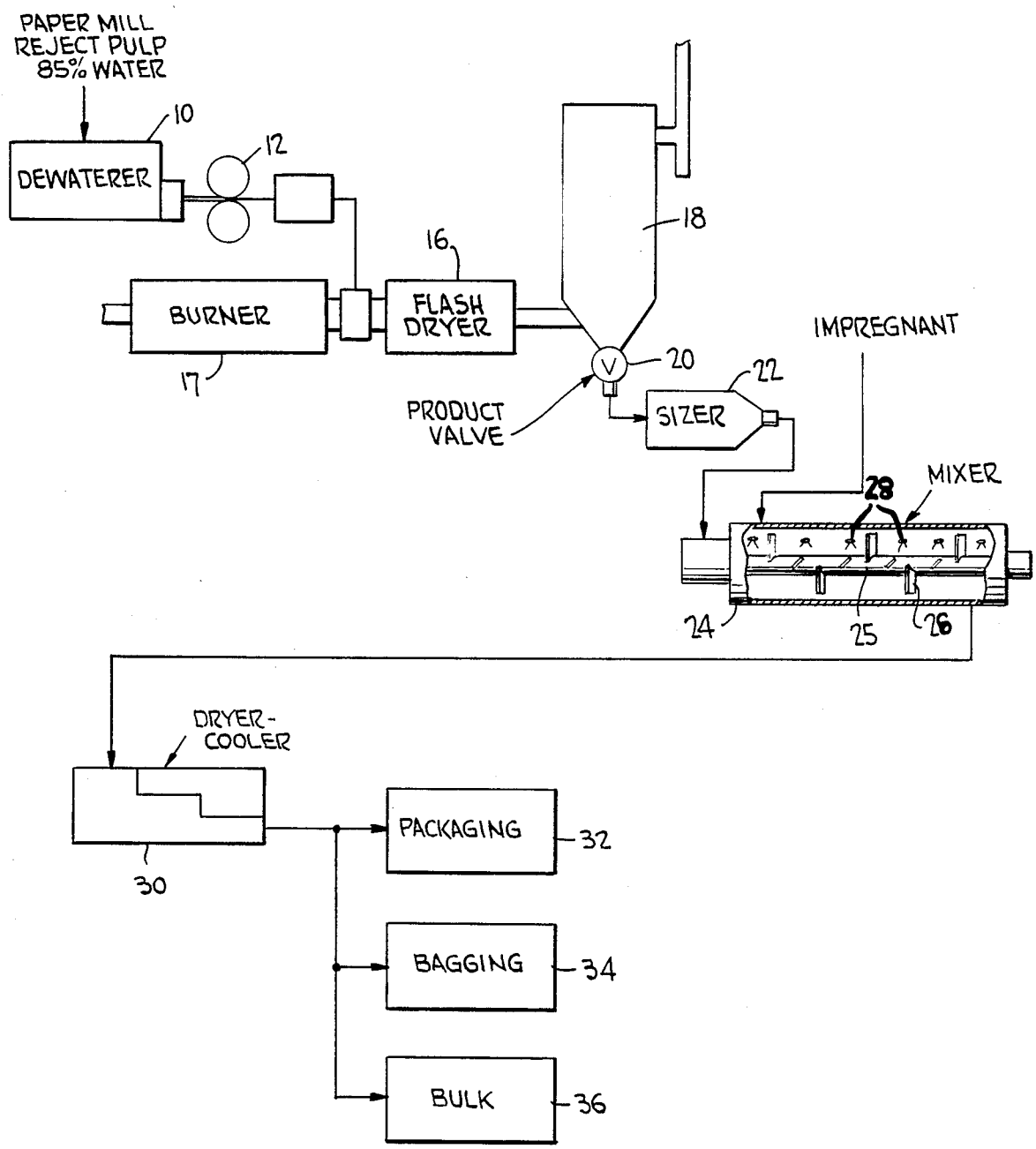

CONTROLLED RELEASE COMPOSITION AND METHOD OF MANUFACTURING SAME

FIELD OF INVENTION AND BACKGROUND

The present invention is directed to controlled release compositions. More particularly, the invention is directed to an expanded, porous, cellulosic carrier material impregnated with an additive material for subsequent release or chemical reaction, and to its process of manufacture. According to the present invention, cellulosic pulp rejects from a papermill are partially dewatered; flash-dried to cause the rejects to expand and become porous; an additive material to be slowly released is applied to the expanded porous cellulosic rejects, and then dried. The cellulosic carrier material holds or retains the additive for delayed release.

It is recognized that there are numerous compositions which are necessarily or most advantageously applied for slow release over a period of time. Such compositions include fertilizers, plant growth stimulants, herbicides, pesticides, and fungicides. As a result of this need, various time or controlled release compositions have been proposed. U.S. Pat. No. 4,388,352 discloses a time-released composition wherein a carrier such as never-dried cellulosic pulp is immersed in a solution of an impregnant, such as a solution of fertilizer; the mixture distilled to exchange the fluid in the pores of the carrier with the solution of the impregnant, and thereafter the carrier is dried to entrap the impregnant within the pores. According to the patent disclosure, during the distillation process the solution of impregnant diffuses through the pulp to displace the water otherwise in the pores. The pulp is then dried. During the drying, the pores of the never-dried pulp irreversibly collapse. The collapse of the pores is the manner in which the impregnant is trapped within the pulp. Accordingly, the carrier material in the final composition is not porous and, therefore, the additive material must pass through the carrier material for release.

U.S. Pat. No. 3,172,752 discloses a controlled release substance having an active material such as a herbicide, fungicide or insecticide suspended in or on perlite as a carrier material which is then coated. In the processing the carrier material is preheated to remove some of the water contained therein. Thereafter, the perlite is heated by means of a hot gas and caused to expand. The expanded perlite particles, according to the patent, provide a relatively inert particulate base for an active material. A holding material is added to the composition so that the additive material will more readily adhere to the perlite base. The holding material can be a material such as lignite, sea kelp, activated sewage sludge, or sulfide paper pulp liquor. Perlite, being a hard glasslike material, has limitations both from the standpoint of its treatment and from its end uses.

U.S. Pat. No. 3,269,824 discloses a wastepaper soil conditioning and fertilizing pellet. According to the patent, wastepaper is repulped and water is then added to it, and the mixture cooked under pressure into a slurry of finely divided cellulose fibers. Fertilizers and other elements are then added to the slurry and thoroughly mixed. The resultant composition is drained into a vacuum chamber where excess moisture is drawn off until the slurry reaches the consistency of a stiff dough. The slurry is then packed into a metal cylinder and extruded into strands which are then cut into pellets. Any moisture remaining in the pellets is removed by drying under infrared lamps as the pellets move from the extrusion step along a conveyor belt. Upon application to soil, the moisture in the soil causes the densified pellets to expand gradually to double or triple their compressed volume while drying of the soil will cause the pellets to contract. The method of manufacture is time-consuming and expensive.

Although the aforesaid methods and compositions are useful and each has certain advantages, none is completely acceptable from the standpoint of cost of materials and processing, stability and structural integrity of the composition, versatility of the carrier material so as to permit the use of a single carrier material for a plurality of additive materials, or availability of the carrier materials in diverse locations so as to permit manufacture of the compositions at or close to the point of use.

OBJECTS AND GENERAL DESCRIPTION OF THE INVENTION

Accordingly, it is a primary object of the present invention to provide a controlled release composition which is low in cost.

It is another primary object of the present invention to provide a controlled release composition having good stability and structural integrity.

It is another object of the present invention to provide a controlled release composition which is versatile permitting the use of a single carrier material for the collection and retaining of a plurality of additive materials.

It is another primary object of the present invention to provide an improved method of making a controlled release composition which is low in cost, has good stability and structural integrity and is versatile in permitting the application and retaining of a variety of additive materials to a carrier using a single process.

These and other objects of the invention will become apparent from the following general description of the invention, the illustrative drawing, and presently preferred detailed embodiment.

According to the present invention, cellulosic pulp rejects normally recovered from a pulpmill in a water slurry are dewatered to remove a part of the water. The partly dewatered pulp rejects are then flash-dried, which expands and renders the rejects porous. In order to get adequate expansion and porosity, it is essential that the cellulosic pulp rejects at the time of flash-drying contain from about 40 to 70% water. The flash-drying is carried out in a conventional louvered rotary dryer such as a Heil or Aeroglide dryer at a temperature of from about 400 to 700° F. The high temperature causes the water on and in the cellulosic rejects to rapidly vaporize, causing the rejects to expand and "explode," providing the desired porosity in the cellulosic carrier. After the flash-drying, the expanded rejects are transferred to a cyclone storage bin from which they are fed to a sizer where they are sized and then fed to a blender. In the blender, the sized rejects are impregnated with an additive material such as a fertilizer. After the impregnation, the impregnated rejects are cooled and subjected to a final drying to the extent necessary. The rejects are then fed to a packaging or bagging machine, or to a bulk storage bin.

According to the presently described invention, the carrier material comprises the cellulosic rejects of a papermaking plant. These rejects are a by-product or waste product of the papermaking operation, and comprise cellulosic fibers which are separated from the main body of pulp during the treatment of the pulp in the papermaking process. These reject fibers are carried in large volumes of water, for example 5% fiber and 95% water. The fibers are separated from the water using filtration means. The separated cellulosic fibers, commonly referred to as "rejects," still contain up to about 85% water. Further, the rejects are in the form of lumps or clumps of fibers. In the flash-drying of the rejects, the lumps or clumps are broken up into small particles. These particles are then impregnated with an additive material without substantial modification of the cellulosic particles. Accordingly, there is an abundant, low-cost supply of carrier material in the vicinity of every papermaking mill.

The additive for application to the cellulosic carrier can be virtually any additive which is compatible with or which can be made compatible with the cellulosic rejects. Cellulosic rejects in water are hydrophilic and, therefore, will accept any naturally hydrophilic additive material or material which has been treated, for example, with a surfactant to provide compatibility. Alternatively, the cellulosic rejects can be treated to render them hydrophobic. The surfactants which are useful include the nonionic, anionic, and cationic surfactants. The selected surfactant depends in part upon the additive material to be utilized. Suitable additives include fertilizers such as mixtures of nitrogen, phosphorus and potash; as well as insecticides, herbicides, fungicides, and plant growth stimulants, particularly those which are to be applied directly to the soil. In such applications not only does the cellulosic carrier slowly release the additive over a period of time, but it acts as well to condition the soil. Over a period of time the carrier is assimilated into the soil to provide for aeration without packing and to help protect against erosion. Other additives for incorporation into the cellulosic rejects include pH-control materials to be used in compositions to be applied to the soil for controlling soil pH or for control of pH in a pH-sensitive operation. For example, the cellulosic carrier can be impregnated with an alkaline material such as sodium hydroxide. The sodium hydroxide containing composition can be used as a barrier for an acid-containing aqueous slurry. As the slurry, for example from an oil well, passes through the barrier, the acid contained in the slurry will be neutralized by the sodium hydroxide in the barrier. As will be apparent to one skilled in the art, other applications can be realized.

DRAWING AND PRESENTLY PREFERRED EMBODIMENT

Having described the invention in general terms, a presently preferred and detailed embodiment will be set forth with reference to the drawing.

In the drawing, the sole figure is a flow diagram of the process for manufacturing the controlled release composition of the present invention. As illustrated in the drawing, papermill reject pulp comprising about 85% water is subjected to a dewatering operation in dewaterer 10 to remove approximately 25% of the total water. Accordingly, the cellulosic rejects after dewatering will contain about 60% total water content. The dewaterer in the embodiment shown comprises a continuously moving web having in association therewith first a pressure roller, a spider mixer, and then a second pressure roller.

Also in the embodiment shown, pulp sizer and conditioner 12 is utilized to treat the dewatered pulp before flash-drying with a nonionic surfactant. A suitable nonionic surfactant is an ethylene oxide derivative of nonylphenol. The conditioned dewatered pulp is then fed to a flash dryer 16 where the cellulose is subjected to a temperature of from about 400 to 700° F., at which temperature the water contained in the reject pulp is rapidly volatilized, expanding the pulp reject and rendering the pulp porous. The flash dryer utilized in the embodiment illustrated is a conventional dryer having a gas burner 17 which permits rapid heating and also heat dissipation.

The flash-dried cellulose rejects are then fed to a cyclone storage bin 18 for storage until the materials are to be impregnated with an additive material. The expanded cellulose is fed from bin 18 through product valve 20 to a sizer 22 where the cellulosic particles are properly sized. It is usually desirable that all of the particles for a particular application have the same size within about a 20% range. Thus, depending upon the end application, one particle size may be preferable over another. For fertilizers it has been found that a preferred size is such that the cellulosic carrier will pass through a Tyler Standard Mesh of 8 to 4. This mesh corresponds to a 3/32 to 3/16 of an inch particle. After the sizing and separation of the different sizes depending upon the application, the cellulosic carrier is fed to a blender. In making a fertilizer, particles having a size of 3/32 to 3/16 of an inch in diameter are fed to blender 24 and kept in continuous motion with an auger 25 having baffles 26. While in continuous motion, the cellulosic particles are sprayed with a aqueous mixture of 20% by weight nitrogen, 20% by weight phosphorus, and 20% by weight potash. As illustrated and in the preferred embodiment, a plurality of sprayers 28—such as an air sprayer having adjustable valves to control the supply of air entering the mixing chamber within the sprayer where air and additive are blended—are arranged along the top or side of the blender. After being impregnated and continuously mixed, the impregnated cellulosic fibers are fed to a dryer-cooler 30, and from the dryer-cooler 30 either to a packaging facility 32, a bagging facility 34, or to bulk storage 36.

The compositions of this invention slowly release the additive material to the environment of use, particularly the soil. Further, the compositions have structural integrity while being stored. They will, however, when applied to the soil become slowly assimilated by the soil, imparting aeration to the soil while helping prevent soil erosion.

As will be apparent to one skilled in the art, various modifications can be made within the scope of the aforesaid description. Such modifications being within the ability of one skilled in the art form a part of the present invention and are embraced by the appended claims.

IT IS CLAIMED:

1. A delayed release composition comprising as a carrier particulate cellulosic pulp rejects which have been expanded and rendered porous by flash-drying pulp rejects having a water content of from about 40 to 70% at a temperature of from about 400 to 700° F.; and, as an additive, up to about 90% of the flash-dried volume of said carrier of an additive material for delayed release distributed on and in said carrier.

2. The composition of claim 1 wherein said carrier includes a conditioner applied thereto prior to flash-drying.

3. The composition of claim 1 wherein said additive material is a fertilizer.

4. The composition of claim 3 wherein said fertilizer is a mixture of nitrogen, phosphorus, and potash.

5. The composition of claim 1 wherein said additive is a fungicide.

6. The composition of claim 1 wherein said additive is an insecticide.

7. The composition of claim 1 wherein said additive is a plant growth stimulant.

8. The composition of claim 1 wherein said additive is a pH-control ingredient.

9. The method of manufacturing a composition for delayed release of an additive material comprising the steps of (1) providing a cellulosic reject pulp having from about 40 to 70% water; (2) flash-drying said reject cellulosic pulp at a temperature of from about 400 to 700° F. to expand and render said particulate rejects porous; (3) impregnating said expanded cellulosic pulp with an additive material; and (4) drying.

10. The method of manufacture of claim 9 including the step of treating said cellulosic pulp reject before flash-drying with a conditioner.

11. The method of claim 10 wherein said conditioner is a surfactant.

12. The method of claim 9 wherein said impregnation is with a blender.

13. The method of claim 9 wherein said additive material is a fertilizer.

14. The method of claim 13 wherein said fertilizer is a mixture of nitrogen, phosphorus, and potash.

15. The method of claim 9 wherein said additive material is an insecticide.

16. The method of claim 9 wherein said additive material is a fungicide.

17. The method of claim 9 wherein said additive material is a plant growth stimulant.

18. The method of claim 9 wherein said additive material is a pH-control ingredient.

* * * * *